United States Patent
Pak et al.

(10) Patent No.: US 8,586,769 B2
(45) Date of Patent: Nov. 19, 2013

(54) CARRIER FOR ETHYLENE OXIDE CATALYSTS

(75) Inventors: Serguei Pak, Teaneck, NJ (US); Andrzej Rokicki, Mountain Lakes, NJ (US); Shuji Kawabata, Aichi (JP); Takayuki Ohashi, Aichi (JP)

(73) Assignees: Scientific Design Company, Inc., Little Ferry, NJ (US); Noritake Co., Limited, Nagoya-shi, Aichi (JP)

( * ) Notice: Subject to any disclaimer, the term of this patent is extended or adjusted under 35 U.S.C. 154(b) by 385 days.

(21) Appl. No.: 12/794,083

(22) Filed: Jun. 4, 2010

(65) Prior Publication Data

US 2011/0301368 A1    Dec. 8, 2011

(51) Int. Cl.
   *C07D 301/03* (2006.01)
   *B01J 23/00* (2006.01)
   *B01J 23/02* (2006.01)
   *B01J 23/48* (2006.01)
   *B01J 23/50* (2006.01)
   *B01J 20/00* (2006.01)
   *B01J 21/04* (2006.01)

(52) U.S. Cl.
   USPC ......... 549/536; 502/347; 502/348; 502/355; 502/415; 502/439

(58) Field of Classification Search
   USPC ......... 502/347, 348, 355, 415, 439; 549/536
   See application file for complete search history.

(56) References Cited

U.S. PATENT DOCUMENTS

| | | | |
|---|---|---|---|
| 3,563,914 A | 2/1971 | Wattimena | |
| 3,702,259 A | 11/1972 | Nielsen | |
| 4,226,782 A | 10/1980 | Hayden et al. | |
| 4,242,235 A | 12/1980 | Cognion et al. | |
| 4,761,394 A | 8/1988 | Lauritzen | |
| 4,766,105 A | 8/1988 | Lauritzen | |
| 4,908,343 A * | 3/1990 | Bhasin | 502/218 |
| 5,011,807 A | 4/1991 | Hayden et al. | |
| 5,057,481 A | 10/1991 | Bhasin | |
| 5,081,096 A * | 1/1992 | Monnier et al. | 502/348 |
| 5,099,041 A | 3/1992 | Hayden et al. | |
| 5,102,848 A | 4/1992 | Soo et al. | |
| 5,112,795 A | 5/1992 | Minahan et al. | |
| 5,187,140 A * | 2/1993 | Thorsteinson et al. | 502/348 |
| 5,266,548 A | 11/1993 | Koradia et al. | |
| 5,380,697 A * | 1/1995 | Matusz et al. | 502/348 |
| 5,395,812 A | 3/1995 | Nagase et al. | |
| 5,407,888 A | 4/1995 | Herzog et al. | |
| 5,418,202 A * | 5/1995 | Evans et al. | 502/348 |
| 5,597,773 A * | 1/1997 | Evans et al. | 502/348 |
| 5,703,253 A * | 12/1997 | Evans et al. | 549/536 |
| 5,801,259 A * | 9/1998 | Kowaleski | 549/536 |
| 5,831,037 A | 11/1998 | Ohsuga et al. | |
| 5,929,259 A * | 7/1999 | Lockemeyer | 549/534 |
| 6,083,870 A * | 7/2000 | Kahn et al. | 502/340 |
| 6,281,370 B1 | 8/2001 | Shima et al. | |
| 6,831,037 B2 * | 12/2004 | Szymanski et al. | 502/355 |
| 7,049,451 B2 * | 5/2006 | Ehara et al. | 549/534 |
| 7,402,612 B2 * | 7/2008 | Jin et al. | 518/713 |
| 7,485,597 B2 * | 2/2009 | Lockemeyer et al. | 502/216 |
| 7,507,844 B2 * | 3/2009 | Pak | 549/534 |
| 7,507,845 B1 * | 3/2009 | Gueckel | 549/536 |
| 7,714,152 B2 * | 5/2010 | Pak | 549/536 |
| 7,825,062 B2 * | 11/2010 | Gerdes et al. | 502/263 |
| 7,910,518 B2 * | 3/2011 | Pak et al. | 502/347 |
| 7,932,408 B2 * | 4/2011 | Guckel | 549/536 |
| 7,977,274 B2 * | 7/2011 | Gueckel | 502/243 |
| 8,084,390 B2 * | 12/2011 | Gerdes et al. | 502/347 |
| 8,349,765 B2 * | 1/2013 | Pak et al. | 502/439 |
| 2003/0125418 A1 * | 7/2003 | Shibusawa et al. | 523/212 |
| 2003/0162984 A1 | 8/2003 | Lockemeyer et al. | |
| 2004/0049061 A1 * | 3/2004 | Lockemeyer et al. | 549/536 |
| 2004/0110973 A1 | 6/2004 | Matusz | |
| 2004/0127586 A1 * | 7/2004 | Jin et al. | 518/715 |
| 2004/0198992 A1 * | 10/2004 | Matusz et al. | 549/533 |
| 2005/0096219 A1 * | 5/2005 | Szymanski et al. | 502/439 |
| 2005/0182172 A1 * | 8/2005 | Kamimura et al. | 524/430 |
| 2006/0252643 A1 | 11/2006 | Pak | |
| 2006/0258532 A1 * | 11/2006 | Thorsteinson et al. | 502/347 |
| 2006/0293180 A1 * | 12/2006 | Thorsteinson | 502/347 |
| 2007/0037991 A1 * | 2/2007 | Rizkalla | 549/533 |
| 2007/0184973 A1 * | 8/2007 | Lockemeyer et al. | 502/200 |
| 2008/0176075 A1 * | 7/2008 | Bauer et al. | 428/402 |
| 2008/0303289 A1 * | 12/2008 | Holliday | 290/4 R |
| 2008/0308528 A1 * | 12/2008 | Wang | 216/53 |
| 2009/0062556 A1 | 3/2009 | Pak | |
| 2009/0177000 A1 * | 7/2009 | Natal et al. | 549/534 |
| 2009/0177016 A1 | 7/2009 | Lockemeyer et al. | |
| 2009/0270249 A1 * | 10/2009 | Dahar et al. | 502/242 |
| 2009/0275763 A1 * | 11/2009 | Serafin et al. | 549/536 |
| 2010/0016617 A1 | 1/2010 | Pak et al. | |
| 2010/0056816 A1 * | 3/2010 | Wallin et al. | 549/534 |
| 2010/0191006 A1 * | 7/2010 | Guckel | 549/536 |

FOREIGN PATENT DOCUMENTS

WO    WO 2010/008920 A2    1/2010

OTHER PUBLICATIONS

International Search Report and Written Opinion dated Feb. 23, 2012 received from the Korean Intellectual Property Office from related International Application No. PCT/US2011/038985.

International Search Report and Written Opinion dated Jul. 2, 2012 received from the Korean Intellectual Property Office from related International Application No. PCT/US2011/061660.

\* cited by examiner

*Primary Examiner* — Cam N. Nguyen

(74) *Attorney, Agent, or Firm* — Scully, Scott, Murphy & Presser, P.C.

(57) ABSTRACT

An improved carrier for an ethylene epoxidation catalyst is provided. The carrier includes an alumina component containing a first portion of alumina particles having a particle size of, or greater than, 3 μm and up to 6 μm, and a second portion of alumina particles having a particle size of, or less than, 2 μm. An improved catalyst containing the above-described carrier, as well as an improved process for the epoxidation of ethylene using the catalyst are also provided.

23 Claims, No Drawings

CARRIER FOR ETHYLENE OXIDE CATALYSTS

FIELD OF THE INVENTION

The present invention relates to silver-based ethylene oxide catalysts, and more particularly, to carriers for such catalysts.

BACKGROUND OF THE INVENTION

As known in the art, high selectivity catalysts (HSCs) for the epoxidation of ethylene refer to those catalysts that possess selectivity values higher than high activity catalysts (HACs) used for the same purpose. Both types of catalysts include silver as the active catalytic component on a refractory support (i.e., carrier). Typically, one or more promoters are included in the catalyst to improve or adjust properties of the catalyst, such as selectivity.

Generally, HSCs achieve the higher selectivity (typically, in excess of 87 mole % or above) by incorporation of rhenium as a promoter. Typically, one or more additional promoters selected from alkali metals (e.g., cesium), alkaline earth metals, transition metals (e.g., tungsten compounds), and main group metals (e.g., sulfur and/or halide compounds) are also included.

There are also ethylene epoxidation catalysts that may not possess the selectivity values typically associated with HSCs, though the selectivity values are improved over HACs. These types of catalysts can also be considered within the class of HSCs, or alternatively, they can be considered to belong to a separate class, e.g., "medium selectivity catalysts" or "MSCs." These types of catalysts typically exhibit selectivities of at least 83 mole % and up to 87 mole %.

In contrast to HSCs and MSCs, the HACs are ethylene epoxidation catalysts that generally do not include rhenium, and for this reason, do not provide the selectivity values of HSCs or MSCs. Typically, HACs include cesium (Cs) as the only promoter.

There has long been an effort to improve the activity and selectivity of ethylene oxidation catalysts. Much of these efforts focus on the compositional and physical characteristics of the carrier (typically alumina), and more particularly, in modifications to the surface area or pore size distribution of the carrier. See, for example, U.S. Pat. Nos. 4,226,782, 4,242,235, 5,266,548, 5,380,697, 5,395,812, 5,597,773, 5,831,037 and 6,831,037 as well as in U.S. Patent Application Publication Nos. 2004/0110973 A1 and 2005/0096219 A1.

Although a higher surface area of the carrier is known to improve catalyst activity, a higher surface area is typically achieved by a concomitant increase in the pore volume contribution of smaller pores (i.e., generally, of or less than 1 micron in size). In turn, the increased amount of smaller pores has a negative effect on the maximum achievable selectivity of the catalyst. Likewise, attempts to improve the selectivity by lowering the volume contribution of smaller pores has the effect of decreasing the surface area of the catalyst, thereby resulting in a decline in the catalyst activity. Thus, there continues to be a long unsolved problem encountered in the art of ethylene oxide catalysts in which improving the activity of the catalyst has a negative impact on the selectivity of the catalyst, and likewise, improving the selectivity has a negative impact on the activity.

Accordingly, there remains a need in the art for improving the catalyst activity while not negatively impacting, or even simultaneously improving, the selectivity of the catalyst. There would be a particular benefit in achieving this by means which are readily integratable into existing process designs, and which are facile and cost effective.

SUMMARY OF THE INVENTION

In one embodiment, the present invention is directed to a carrier for an ethylene epoxidation catalyst. The carrier contains an alumina component which contains a first portion of alumina particles having a particle size of, or greater than, 3 µm and up to 6 µm, and a second portion of alumina particles having a particle size of, or less than, 2 µm. By including the foregoing combination of larger and smaller carrier particles, the surface area of the carrier can be adjusted independently from surface area changes attributable to the pore size distribution of the carrier particles. Because of this, a high enough surface area (i.e., to suitably increase catalyst activity) in the carrier can be achieved without increasing the pore volume contribution of smaller pore sizes (generally of, or less than, 1 micron) to a point which has a deleterious effect on selectivity. Accordingly, the invention advantageously provides a carrier which can be used to prepare an ethylene oxidation catalyst having an increased catalyst activity and a maintained or improved selectivity.

The invention is also directed to an ethylene oxidation (i.e., epoxidation) catalyst comprising the carrier described above, along with a catalytic amount of silver, and preferably, a promoting amount of rhenium deposited on and/or in the carrier.

The invention is also directed to a method for the vapor phase conversion of ethylene to ethylene oxide (EO) in the presence of oxygen. The method includes reacting a reaction mixture comprising ethylene and oxygen in the presence of the ethylene epoxidation catalyst described above.

DETAILED DESCRIPTION OF THE INVENTION

In one aspect, the invention is directed to an improved carrier (i.e., support) for an ethylene epoxidation catalyst. The carrier contains an alumina component which includes a larger particle size component (i.e., a coarser component) and a smaller particle size component (i.e., a finer component) suitably adjusted, as further described below, to provide the resulting epoxidation catalyst with an increased activity while maintaining or improving the selectivity, or conversely, an improved selectivity while maintaining or improving the activity.

Preferably, the alumina component contains a first portion of alumina particles having a particle size of, or greater than, 3 µm and up to 6 µm, and a second portion of alumina particles having a particle size of, or less than, 2 µm. In different embodiments, the first portion of alumina particles can have a particle size of, for example, 3 µm, 3.1 µm, 3.2 µm, 3.3 µm, 3.4 µm, 3.5 µm, 3.6 µm, 3.7 µm, 3.8 µm, 3.9 µm, 4 µm, 4.1 µm, 4.2 µm, 4.3 µm, 4.4 µm, 4.5 µm, 4.6 µm, 4.7 µm, 4.8 µm, 4.9 µm, 5 µm, 5.1 µm, 5.2 µm, 5.3 µm, 5.4 µm, 5.5 µm, 5.6 µm, 5.7 µm, 5.8 µm, 5.9 µm, or 6 µm, or a particular range between any two of these values (for example, 3-5 µm, 3-5.5 µm, 3-4 µm, 4-6 µm, or 5-6 µm). In different embodiments, the second portion of alumina particles can have a particle size of, or less than, for example, 2 µm, 1.9 µm, 1.8 µm, 1.7 µm, 1.6 µm, 1.5 µm, 1.4 µm, 1.3 µm, 1.2 µm, 1.1 µm, 1 µm, 0.9 µm, 0.8 µm, 0.7 µm, 0.6 µm, 0.5 µm, 0.4 µm, 0.3 µm, 0.2 µm, or 0.1 µm, or a particular range between any two of these values (for example, 0.1-2 µm, 0.1-1.5 µm, 0.1-1 µm, 0.1-0.8 µm, 0.1-0.6 µm, 0.2-2 µm, 0.2-1.5 µm, 0.2-1 µm, 0.2-0.8 µm, 0.2-0.6 µm, 0.3-2 µm, 0.3-1.5 µm, 0.3-1 µm, 0.3-0.8 µm, 0.3-0.6 µm, 0.4-2 µm, 0.4-1.5 µm, 0.4-1 µm, 0.4-0.8 µm, or 0.4-0.6 µm).

The particle sizes given above can refer to a diameter for the case where the particle is spherical or approximately spherical. For cases where the particles substantially deviate from a spherical shape, the particle sizes given above are based on the equivalent diameter of the particles. As known in the art, the term "equivalent diameter" is used to express the size of an irregularly-shaped object by expressing the size of the object in terms of the diameter of a sphere having the same volume as the irregularly-shaped object.

At least the first portion of alumina particles (i.e., larger particles of 3-6 μm) and second portion of alumina particles (i.e., smaller particles of or less than 2 μm) are required to be present in the carrier, i.e., the first portion of alumina particles is not in an amount of 100 weight percentage (wt %) and the second portion of alumina particles is not in an amount of 100 wt % (wherein the foregoing wt % is relative to the weight of the alumina component of the carrier). In different embodiments, the first portion or the second portion of alumina particles is in an amount of at least 1 wt %, 2 wt %, 5 wt %, 20 wt %, 25 wt %, 30 wt %, 40 wt %, 50 wt %, 60 wt %, 70 wt %, 80 wt %, 90 wt %, 95 wt %, 98 wt %, or 99 wt %, or within a weight percentage (wt %) range bounded by any of the foregoing values. In one embodiment, the alumina component contains only a first portion and a second portion of alumina particles, such that a wt % A of one portion of alumina particles necessarily indicates that the other portion has a wt % of 100-A. In another embodiment, the alumina component contains one or more other portions of alumina particles (e.g., a third portion) which do not have a particle size within the broadest ranges set forth for the first and second portions of alumina particles, as given above. In this case, a wt % A of the first portion of alumina particles does not correspond to a wt % of 100-A for the second portion of alumina particles. Preferably, one or more other portions of alumina particles (i.e., outside of the particle size ranges of the first and second portions of alumina particles) have a wt % of less than 50 wt %, 40 wt %, 30 wt %, 25 wt %, 20 wt %, 15 wt %, 10 wt %, 5 wt %, 2 wt %, 1 wt %, 0.5 wt %, 0.2 wt %, or 0.1 wt %.

The alumina particles are preferably composed of any of the refractory alumina compositions known in the art for use in ethylene oxidation catalysts. Preferably, the alumina is alpha-alumina. The alpha-alumina used in the inventive carrier preferably has a very high purity, i.e., about 95% or more, and more preferably, 98 wt. % or more alpha-alumina. Preferably, the alpha-alumina is a low sodium alumina or a low sodium reactive alumina. The term "reactive alumina" as used herein generally indicates an alpha-alumina with good sinterability and having a particle size that is very fine, i.e., generally, of 2 microns or less. Generally, a "low sodium alumina" material contains 0.1% or less sodium content. Alternatively, or in addition, a "low sodium alumina" can indicate an alumina material having 0.1 mg or less of sodium. Good sinterability is generally derived from a 2 micron or less particle size.

Remaining components may be other phases of alumina, silica, alkali metal oxides (e.g., sodium oxide) and trace amounts of other metal-containing and/or non-metal-containing additives or impurities. Suitable alumina compositions are manufactured and/or commercially available from, for example, Noritake of Nagoya, Japan, and the NorPro Company of Akron, Ohio.

The carrier can optionally contain a stability-enhancing amount of mullite to provide an epoxidation catalyst with an improved stability and/or selectivity. As used herein, "mullite" (also known as "porcelainite") refers to an aluminum silicate mineral having an $Al_2O_3$ component combined as a solid solution with a $SiO_2$ phase, wherein the $Al_2O_3$ component is present in a concentration of at least about 40 mole percent and typically up to about 80 mole percent. More typically, mullite contains the $Al_2O_3$ component in a concentration of 60±5 mole percent, which can thus be approximately represented by the formula $3Al_2O_3.2SiO_2$ (i.e., $Al_6Si_2O_{13}$).

Since natural sources of mullite are scarce, most commercial sources of mullite are synthetic. A variety of synthetic methods are known in the art for the production of mullite. In one embodiment, the mullite used contains no other component other than the alumina and silica components described above, except for one or more components that may be present in trace amounts (e.g., less than 0.1 mole or weight percent). In another embodiment, the mullite used can include one or more additional components. For example, sodium oxide ($Na_2O$) can be included in a minor amount (typically no more than about 1.0 mole or weight percent). Other components, such as zirconia ($Zr_2O$) or silicon carbide (SiC) can also be included to, for example, increase fracture toughness. Numerous other metal oxides can also be incorporated to alter the properties of the mullite.

A stability-enhancing amount of mullite is typically at least about 0.5 wt % and up to about 20 wt % of mullite by total weight of the carrier. In one embodiment, the mullite is present in the carrier in a concentration of at least about 1 wt % and up to about 20 wt %, 15 wt %, 12 wt %, 10 wt %, 8 wt %, 6 wt %, 5 wt %, 4 wt %, 3 wt %, or 2 wt % by total weight of the carrier. In another embodiment, the mullite is present in the carrier in a concentration of at least about 3 wt % and up to about 20 wt %, 15 wt %, 12 wt %, 10 wt %, 8 wt %, 6 wt %, 5 wt %, or 4 wt % by total weight of the carrier. In yet another embodiment, the mullite is present in the carrier in a concentration of at least about 5 wt % and up to about 20 wt %, 15 wt %, 12 wt %, 10 wt %, 8 wt %, 7 wt %, or 6 wt % by total weight of the carrier. In still another embodiment, the mullite is present in the carrier in a concentration of at least about 7 wt % and up to about 20 wt %, 15 wt %, 12 wt %, 10 wt %, 9 wt %, or 8 wt % by total weight of the carrier. In still other embodiments, the mullite can be present in the carrier within a concentration range of about 0.5-15 wt %, 0.5-12 wt %, 0.5-10 wt %, 0.5-8 wt %, 0.5-6 wt %, 0.5-5 wt %, 0.5-3 wt %, 0.5-2 wt %, 10-20 wt %, or 10-15 wt % by total weight of the carrier.

In one embodiment, the outer surface of the bulk alumina carrier or the alumina particles themselves are coated with mullite. The outer surface may be coated in conjunction with subsurface or interior portions of the carrier also containing mullite, or alternatively, in the absence of either subsurface or interior portions containing mullite. In another embodiment, the outer surface of the alumina carrier or the alumina particles themselves are not coated with mullite while either a subsurface or interior region of the carrier contains mullite.

In general, a suitable catalyst carrier is prepared by a procedure in which the alumina of various particle sizes, and optionally, mullite particles, become bonded together by a bonding agent. For example, a suitable catalyst carrier can be prepared by combining the alumina component, mullite component, a solvent such as water, a temporary binder or burnout material, a permanent binder, and/or a porosity controlling agent, and then firing (i.e., calcining) the mixture by methods well known in the art.

Temporary binders, or burnout materials, include cellulose, substituted celluloses, e.g., methylcellulose, ethylcellulose, and carboxyethylcellulose, stearates (such as organic stearate esters, e.g., methyl or ethyl stearate), waxes, granulated polyolefins (e.g., polyethylene and polypropylene), walnut shell flour, and the like, which are decomposable at the temperatures employed. The binders are responsible for imparting porosity to the carrier material. Burnout material is used primarily to ensure the preservation of a porous structure during the green (i.e., unfired phase) in which the mixture may be shaped into particles by molding or extrusion processes. Burnout materials are essentially completely removed during the firing to produce the finished carrier.

The carriers of the invention are preferably prepared by the inclusion of a binder material in sufficient amount to substantially prevent the formation of crystalline silica compounds. Permanent binders include, for example, inorganic clay-type materials, such as silica and an alkali metal compound. A convenient binder material which may be incorporated with the alumina particles is a mixture of boehmite, an ammonia-stabilized silica sol, and a soluble sodium salt.

The formed paste is extruded or molded into the desired shape and fired at a temperature typically from about 1200° C. to about 1600° C. to form the carrier. In embodiments in which the particles are formed by extrusion, it may be desirable to include conventional extrusion aids. Generally, the performance of the carrier is enhanced if it is treated by soaking the carrier in a solution of an alkali hydroxide, such as sodium hydroxide, potassium hydroxide, or an acid such as $HNO_3$ as described in U.S. Patent Application Publication No. 2006/0252643 A1. After treatment, the carrier is preferably washed, such as with water, to remove unreacted dissolved material and treating solution, and then optionally dried.

The carrier of the invention is preferably porous and typically has a B.E.T. surface area of at most 20 $m^2/g$. The B.E.T. surface area is more typically in the range of about 0.1 to 10 $m^2/g$, and more typically from 1 to 5 $m^2/g$. In other embodiments, the carriers of the invention are characterized by having a B.E.T. surface area from about 0.3 $m^2/g$ to about 3 $m^2/g$, preferably from about 0.6 $m^2/g$ to about 2.5 $m^2/g$, and more preferably from about 0.7 $m^2/g$ to about 2.0 $m^2/g$. The B.E.T. surface area described herein can be measured by any suitable method, but is more preferably obtained by the method described in Brunauer, S., et al., *J. Am. Chem. Soc.*, 60, 309-16 (1938). The final support typically possesses a water absorption value ranging from about 0.2 cc/g to about 0.8 cc/g, and more typically from about 0.25 cc/g to about 0.6 cc/g.

The carrier can have any suitable distribution of pore diameters. As used herein, the "pore diameter" is used interchangeably with "pore size". The pore volume (and pore size distribution) described herein can be measured by any suitable method, but are more preferably obtained by the conventional mercury porosimeter method as described in, for example, Drake and Ritter, *Ind. Eng. Chem. Anal. Ed.*, 17, 787 (1945).

Preferably, the pore diameters are at least about 0.01 microns (0.01 μm), and more typically, at least about 0.1 μm. In yet different embodiments, the pore diameters are at least about 0.2 μm, 0.3 μm, 0.4 μm, 0.5 μm, 0.6 μm, 0.7 μm, 0.8 μm, 0.9 μm, 1.0 μm, 1.2 μm, 1.4 μm, 1.6 μm, or 1.8 μm. In different embodiments, the pore diameters are no more than about 2.0 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, or 10.5 μm. Any range derived from the foregoing minimum and maximum exemplary values is also suitable herein.

In different embodiments, the percentage of pores having a size of or less than 1 μm, 1.5 μm, or 2 μm is no more than 40%, 35%, 30%, 25%, 20%, 15%, 10%, 5%, 2%, or 1%, or a range between any two of these values. In other embodiments, no more than 20%, 15%, 10%, 5%, 2%, or 1% of the pores have a size greater than 2 μm. In particular embodiments, at least 50%, 60%, 70%, 80%, 90%, or 95% of the pores have a size within 0.1-3 μm, 0.5-3 μm, 0.1-2.5 μm, 0.5-2.5 μm, 0.1-2 μm, 0.5-2 μm, or 1-2 μm.

The carrier typically possesses a pore size distribution (e.g., within a range as set forth above) characterized by the presence of one or more pore sizes of peak concentration, i.e., one or more maxima (where the slope is approximately zero) in a pore size vs. number of pores distribution plot. A pore size of maximum concentration is also referred to herein as a peak pore size, peak pore volume, or peak pore concentration. In a preferred embodiment, the pore size distribution is characterized by the presence of a peak pore size of or less than 2 μm. In different embodiments, the pore size distribution contains a peak pore size of about 2 μm, 1.8 μm, 1.6 μm, 1.4 μm, 1.2 μm, 1.0 μm, 0.8 μm, 0.7 μm, 0.6 μm, 0.5 μm, 0.4 μm, 0.3 μm, 0.2 μm, or 0.1 μm, or within a particular range bounded by any two of the foregoing values.

Furthermore, each pore size distribution can be characterized by a single mean pore size (mean pore diameter) value. Accordingly, a mean pore size value given for a pore size distribution necessarily corresponds to a range of pore sizes that results in the indicated mean pore size value. Any of the exemplary pore sizes given above can alternatively be understood to indicate a mean (i.e., average or weighted average) pore size.

In a particular embodiment, the carrier possesses a multimodal pore size distribution within any of the pore size ranges described above. The multimodal pore size distribution is characterized by the presence of different pore sizes of peak concentration (i.e., different peak pore sizes) in a pore size vs. number of pores distribution plot. The different peak pore sizes are preferably within the range of pore sizes given above. Each peak pore size can be considered to be within its own pore size distribution (mode), i.e., where the pore size concentration on each side of the distribution falls to approximately zero (in actuality or theoretically). The multimodal pore size distribution can be, for example, bimodal, trimodal, or of a higher modality. In one embodiment, different pore size distributions, each having a peak pore size, are non-overlapping by being separated by a concentration of pores of approximately zero (i.e., at baseline). In another embodiment, different pore size distributions, each having a peak pore size, are overlapping by not being separated by a concentration of pores of approximately zero.

In a particular embodiment, the mean pore diameter of a first mode of pores and the mean pore diameter of a second mode of pores (i.e., the "differential in mean pore diameters") in a multimodal pore size distribution are different by at least about 0.1 μm. In different embodiments, the difference in mean pore sizes can be at least, for example, 0.2 μm, or 0.3 μm, or 0.4 μm, or 0.5 μm, or 0.6 μm, or 0.7 μm, or 0.8 μm, or 0.9 μm, or 1.0 μm, or 1.2 μm, or 1.4 μm, or 1.5 μm, 1.6 μm, or 1.8 μm, or 2.0 μm.

The carrier of the invention can be of any suitable shape or morphology. For example, the carrier can be in the form of particles, chunks, pellets, rings, spheres, three-holes, wagon wheels, cross-partitioned hollow cylinders, and the like, of a size preferably suitable for employment in fixed bed reactors.

In one embodiment, the carrier of the invention contains essentially only alumina, or alumina and mullite components, in the absence of other metals or chemical compounds, except that trace quantities of other metals or compounds may be present. A trace amount is an amount low enough that the trace species does not observably affect functioning or ability of the catalyst.

In another embodiment, the carrier of the invention contains one or more promoting species. As used herein, a "promoting amount" of a certain component of a catalyst refers to an amount of that component that works effectively to provide an improvement in one or more of the catalytic properties of the catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement is exhibited in the activity rather than in the selectivity.

For example, the inventive carrier may include a promoting amount of an alkali metal or a mixture of two or more alkali metals. Suitable alkali metal promoters include, for example, lithium, sodium, potassium, rubidium, cesium or combinations thereof. Cesium is often preferred, with combinations of cesium with other alkali metals also being preferred. The amount of alkali metal will typically range from about 10 ppm to about 3000 ppm, more typically from about 15 ppm to about 2000 ppm, more typically from about 20 ppm to about 1500 ppm, and even more typically from about 50 ppm to about 1000 ppm by weight of the total catalyst, expressed in terms of the alkali metal.

The carrier of the invention may also include a promoting amount of a Group IIA alkaline earth metal or a mixture of two or more Group IIA alkaline earth metals. Suitable alkaline earth metal promoters include, for example, beryllium, magnesium, calcium, strontium, and barium or combinations thereof. The amounts of alkaline earth metal promoters are used in similar amounts as the alkali metal promoters described above.

The carrier of the invention may also include a promoting amount of a main group element or a mixture of two or more main group elements. Suitable main group elements include any of the elements in Groups IIIA (boron group) to VIIA (halogen group) of the Periodic Table of the Elements. For example, the catalyst can include a promoting amount of one or more sulfur compounds, one or more phosphorus compounds, one or more boron compounds, one or more halogen-containing compounds, or combinations thereof. The catalyst can also include a main group element, aside from the halogens, in its elemental form.

The carrier of the invention may also include a promoting amount of a transition metal or a mixture of two or more transition metals. Suitable transition metals can include, for example, the elements from Groups IIIB (scandium group), IVB (titanium group), VB (vanadium group), VIB (chromium group), VIIB (manganese group), VIIIB (iron, cobalt, nickel groups), IB (copper group), and IIB (zinc group) of the Periodic Table of the Elements, as well as combinations thereof. More typically, the transition metal is an early transition metal, i.e., from Groups IIIB, IVB, VB or VIB, such as, for example, hafnium, yttrium, molybdenum, tungsten, rhenium, chromium, titanium, zirconium, vanadium, tantalum, niobium, or a combination thereof.

The carrier of the invention may also include a promoting amount of a rare earth metal or a mixture of two or more rare earth metals. The rare earth metals include any of the elements having an atomic number of 57-103. Some examples of these elements include lanthanum (La), cerium (Ce), and samarium (Sm).

The transition metal or rare earth metal promoters are typically present in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of total catalyst, expressed in terms of the metal.

All of these promoters, aside from the alkali metals, can be in any suitable form, including, for example, as zerovalent metals or higher valent metal ions.

Of the promoters listed, rhenium (Re) is preferred as a particularly efficacious promoter for ethylene epoxidation high selectivity catalysts. The rhenium component in the catalyst can be in any suitable form, but is more typically one or more rhenium-containing compounds (e.g., a rhenium oxide) or complexes. The rhenium can be present in an amount of, for example, about 0.001 wt. % to about 1 wt. %. More typically, the rhenium is present in amounts of, for example, about 0.005 wt. % to about 0.5 wt. %, and even more typically, from about 0.01 wt. % to about 0.05 wt. % based on the weight of the total catalyst including the support, expressed as rhenium metal.

In another aspect, the invention is directed to an ethylene epoxidation catalyst produced from the carrier described above. In order to produce the catalyst, a carrier having the above characteristics is then provided with a catalytically effective amount of silver thereon and/or therein. The catalysts are prepared by impregnating the carriers with silver ions, compounds, complexes, and/or salts dissolved in a suitable solvent sufficient to cause deposition of a silver precursor compound onto and/or into the carrier. The carrier can be impregnated and incorporated with rhenium and silver, along with any desired promoters, by any of the conventional methods known in the art, e.g., by excess solution impregnation, incipient wetness impregnation, spray coating, and the like. Typically, the carrier material is placed in contact with the silver-containing solution until a sufficient amount of the solution is absorbed by the carrier. Preferably, the quantity of the silver-containing solution used to impregnate the carrier is no more than is necessary to fill the pore volume of the carrier. Infusion of the silver-containing solution into the carrier can be aided by application of a vacuum. A single impregnation or a series of impregnations, with or without intermediate drying, may be used, depending in part on the concentration of the silver component in the solution. Impregnation procedures are described in, for example, U.S. Pat. Nos. 4,761,394, 4,766,105, 4,908,343, 5,057,481, 5,187,140, 5,102,848, 5,011,807, 5,099,041 and 5,407,888, all of which are incorporated herein by reference. Known procedures for pre-deposition, co-deposition, and post-deposition of the various promoters can also be employed.

Silver compounds useful for impregnation include, for example, silver oxalate, silver nitrate, silver oxide, silver carbonate, a silver carboxylate, silver citrate, silver phthalate, silver lactate, silver propionate, silver butyrate and higher fatty acid salts and combinations thereof. The silver solution used to impregnate the carrier can contain any suitable solvent. The solvent can be, for example, water-based, organic-based, or a combination thereof. The solvent can have any suitable degree of polarity, including highly polar, moderately polar or non-polar, or substantially or completely non-polar. The solvent typically has sufficient solvating power to solubilize the solution components. Some examples of water-based solvents include water and water-alcohol mixtures. Some examples of organic-based solvents include, but are not limited to, alcohols (e.g., alkanols), glycols (e.g., alkyl glycols), ketones, aldehydes, amines, tetrahydrofuran, nitrobenzene, nitrotoluene, glymes (e.g., glyme, diglyme and tetraglyme), and the like, and their combinations. Organic-based solvents that have 1 to about 8 carbon atoms per molecule are preferred.

A wide variety of complexing or solubilizing agents may be employed to solubilize silver to the desired concentration in the impregnating medium. Useful complexing or solubilizing agents include amines, ammonia, lactic acid and combinations thereof. For example, the amine can be an alkylene diamine having from 1 to 5 carbon atoms. In a preferred embodiment, the solution comprises an aqueous solution of silver oxalate and ethylene diamine. The complexing/solubilizing agent may be present in the impregnating solution in an amount from about 0.1 to about 5.0 moles of ethylene diamine per mole of silver, preferably from about 0.2 to about 4.0 moles, and more preferably from about 0.3 to about 3.0 moles of ethylene diamine for each mole of silver.

The concentration of silver salt in the solution is typically in the range from about 0.1% by weight to the maximum permitted by the solubility of the particular silver salt in the solubilizing agent employed. More typically, the concentration of silver salt is from about 0.5% to 45% by weight of silver, and even more typically, from about 5 to 35% by weight.

The ethylene oxide (EO) catalyst contains a catalytically effective amount of silver metal to catalyze the synthesis of ethylene oxide from ethylene and oxygen. The silver can be located on the surface and/or throughout the pores of the refractory support. A catalytically effective amount of silver can be, for example, up to about 45% by weight of silver, expressed as metal, based on the total weight of the catalyst including the support. Silver contents, expressed as metal, of from about 1% to about 40% based on the total weight of the catalyst are more typical. In other embodiments, the silver content can be from, for example, about 1 to 35%, 5 to 35%, 1 to 30%, 5 to 30%, 1 to 25%, 5 to 25%, 1 to 20%, 5 to 20%, 8 to 40%, 8 to 35%, 8 to 30%, 10 to 40%, 10 to 35%, 10 to 25%, 12 to 40%, 12 to 35%, 12 to 30%, or 12 to 25%.

Rhenium is also preferably incorporated into the silver-containing catalyst in order to provide a high selectivity catalyst. The rhenium is incorporated in the promoting amounts described above either prior to (i.e., by prior incorporation into the carrier), coincidentally with, or subsequent to the deposition of the silver.

Any one or more other promoting species can also be incorporated into the carrier either prior to, coincidentally with, or subsequent to the deposition of the silver. In one preferred embodiment, additional promoters include one or more species selected from Cs, Li, W, F, P, Ga, and S. In another preferred embodiment, additional promoters include one or more species selected from Cs, Li, and S.

After impregnation with silver and any promoters, the impregnated carrier is removed from the solution and calcined for a time sufficient to reduce the silver component to metallic silver and to remove volatile decomposition products from the silver-containing support. The calcination is typically accomplished by heating the impregnated carrier, preferably at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a reaction pressure in a range from about 0.5 to about 35 bar. In general, the higher the temperature, the shorter the required calcination period. A wide range of heating periods have been described in the art for the thermal treatment of impregnated supports. See, for example, U.S. Pat. No. 3,563,914, which indicates heating for less than 300 seconds, and U.S. Pat. No. 3,702,259, which discloses heating from 2 to 8 hours at a temperature of from 100° C. to 375° C. to reduce the silver salt in the catalyst. A continuous or step-wise heating program may be used for this purpose.

During calcination, the impregnated support is typically exposed to a gas atmosphere comprising an inert gas, such as nitrogen. The inert gas may also include a reducing agent.

In another aspect, the invention is directed to a method for the vapor phase production of ethylene oxide by conversion of ethylene to ethylene oxide in the presence of oxygen by use of the catalyst described above. Generally, the ethylene oxide production process is conducted by continuously contacting an oxygen-containing gas with ethylene in the presence of the catalyst at a temperature in the range from about 180° C. to about 330° C., more typically from about 200° C. to about 325° C., and more typically from about 225° C. to about 270° C., at a pressure which may vary from about atmospheric pressure to about 30 atmospheres depending on the mass velocity and productivity desired. Pressures in the range of from about atmospheric to about 500 psi are generally employed. Higher pressures may, however, be employed within the scope of the invention. Residence times in large-scale reactors are generally on the order of about 0.1 to about 5 seconds. A typical process for the oxidation of ethylene to ethylene oxide comprises the vapor phase oxidation of ethylene with molecular oxygen in the presence of the inventive catalyst in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with catalyst.

The inventive catalysts have been shown to be particularly selective catalysts in the oxidation of ethylene with molecular oxygen to ethylene oxide. The conditions for carrying out such an oxidation reaction in the presence of the catalyst of the present invention broadly comprise those described in the prior art. This applies, for example, to suitable temperatures, pressures, residence times, diluent materials (e.g., nitrogen, carbon dioxide, steam, argon, methane or other saturated hydrocarbons), the presence or absence of moderating agents to control the catalytic action (e.g., 1,2-dichloroethane, vinyl chloride or ethyl chloride), the desirability of employing recycle operations or applying successive conversion in different reactors to increase the yields of ethylene oxide, and any other special conditions which may be selected in processes for preparing ethylene oxide. Molecular oxygen employed as a reactant may be obtained from conventional sources. The suitable oxygen charge may be relatively pure oxygen, or a concentrated oxygen stream comprising oxygen in a major amount with lesser amounts of one or more diluents such as nitrogen or argon, or air.

In the production of ethylene oxide, reactant feed mixtures typically contain from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or by-products, unreacted materials are typically returned to the oxidation reactor. For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-

315° C., an oxygen conversion level of 10-60%, and an EO production (work rate) of 100-300 kg EO per cubic meters of catalyst per hour. Typically, the feed composition at the reactor inlet comprises 1-40% ethylene, 3-12% oxygen, 0.3-40% $CO_2$, 0-3% ethane, 0.3-20 ppmv total concentration of organic chloride moderator, and the balance of the feed comprised of argon, methane, nitrogen, or mixtures thereof.

In other embodiments, the process of ethylene oxide production includes the addition of oxidizing gases to the feed to increase the efficiency of the process. For example, U.S. Pat. No. 5,112,795 discloses the addition of 5 ppm of nitric oxide to a gas feed having the following general composition: 8 volume % oxygen, 30 volume % ethylene, about 5 ppmw ethyl chloride, and the balance nitrogen.

The resulting ethylene oxide is separated and recovered from the reaction products using methods known in the art. The ethylene oxide process may include a gas recycle process wherein a portion or substantially all of the reactor effluent is readmitted to the reactor inlet after substantially or partially removing the ethylene oxide product and any byproducts. In the recycle mode, carbon dioxide concentrations in the gas inlet to the reactor may be, for example, from about 0.3 to about 6 volume percent.

Examples have been set forth below for the purpose of further illustrating the invention. The scope of this invention is not to be in any way limited by the examples set forth herein.

EXAMPLE 1

Synthesis of Alumina-Based Porous Supports 70 parts by weight of low sodium alumina secondary particles, 20 parts by weight of fine alumina particles, and 10 parts by weight of mullite-based inorganic binder were mixed to obtain an alumina raw material. The low sodium alumina secondary particles contained 99.0% or more of $Al_2O_3$, and had a median particle diameter of 40 μm, (mean diameter of 30 to 70 μm, surface area of 0.5 to 20 $m^2/g$, an α-alumina crystal size of 1 to 5 μm, $Na_2O$ content of 0.1% or less). The fine alumina particle contained 99.0% or more of $Al_2O_3$, and had a mean particle diameter of 0.5 μm, (mean diameter of 0.2 to 20 μm, surface area of 5 to 100 $m^2/g$, an α-alumina crystal size of less than 0.5 μm, $Na_2O$ content of 0.1% or less). The mullite-based inorganic binder had a particle size of 10 μm or less, and was present in an amount of 10% of the entire weight.

To 100 parts by weight of the alumina raw material, 1.0 part by weight of microcrystalline cellulose and 10 parts by weight of wax emulsion were added as molding aids and organic binders, together with 5 parts by weight of walnut powder as a pore-forming agent, along with 28 parts by weight of water. The resulting mixture was blended by means of a kneading instrument, and then extruded to obtain a hollow tube molded body with 8 mm in the external diameter, 4 mm in the internal diameter and 8 mm in the length. The extruded blend was dried for 2 hours at 60 to 100° C., and then placed in a refractory saggar. The saggar consisted of a sintering setter loaded with a sintering frame. The extruded blend was then subjected to a firing process by use of a roller hearth kiln. In the firing process, the extruded blend was subjected to the maximum sintering temperature (e.g., in particular embodiments, up to 1600° C.) for 2 hours and then held at 1400° C. for 0.5 hours.

The resulting support possessed a surface area of 0.9 $m^2/g$, water absorption ratio of 32%, and apparent porosity of 55%. The total volume of micropores was found to be 0.35 mL. The peak of pore volume distribution was found to be about 1.5 μm. The amount of pores in the range of 1 to 2 μm was 47%, while the amount of pores in the range less than 1 μm was less than 35%.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein.

What is claimed is:

1. A carrier for an ethylene epoxidation catalyst, the carrier comprising alumina containing a first portion of alumina particles having a particle size of, or greater than, 3 μm and up to 6 μm, and a second portion of alumina particles having a particle size less than 1 μm, wherein at least 20 wt% but less than 100 wt% of the alumina particles have said particle size less than 1 μm, wherein said wt% is relative to the weight of alumina in the carrier.

2. The carrier according to claim 1, wherein the first portion of alumina particles has a particle size of, or greater than, 3 μm and up to 5 μm.

3. The carrier according to claim 1, wherein at least 20 wt% but less than 100 wt% of the alumina particles have a particle size of, or less than, 2μm, wherein said wt% is relative to the weight of alumina in the carrier.

4. The carrier according to claim 1, wherein the alumina is a-alumina.

5. The carrier according to claim 1, further comprising a stability-enhancing amount of mullite.

6. The carrier according to claim 5, wherein the stability-enhancing amount of mullite is about 0.5-20 wt% mullite by total weight of the carrier.

7. The carrier according to claim 5, wherein the stability-enhancing amount of mullite is about 1-15% mullite by total weight of the carrier.

8. The carrier according to claim 5, wherein the stability-enhancing amount of mullite is about 3-12% mullite by total weight of the carrier.

9. The carrier according to claim 1, further comprising a promoting amount of rhenium.

10. The carrier according to claim 1, further comprising a promoting amount of an alkali or alkaline earth metal.

11. The carrier according to claim 1, further comprising a promoting amount of cesium.

12. The carrier according to claim 1, wherein the carrier possesses a pore size distribution having a peak pore size of, or less than, 2 μm.

13. The carrier according to claim 1, wherein no more than 40% of the pores have a pore size of or less than 1 μm.

14. An ethylene epoxidation catalyst comprising:
   a) a carrier comprising alumina containing a first portion of alumina particles having a particle size of, or greater than, 3 μm and up to 6 μm, and a second portion of alumina particles having a particle size less than 1 μm, wherein at least 20 wt% but less than 100 wt% of the alumina particles have said particle size less than 1 μm, wherein said wt% is relative to the weight of alumina in the carrier;
   b) a catalytic amount of silver deposited on and/or in said carrier; and
   c) a promoting amount of rhenium deposited on and/or in said carrier.

15. The catalyst according to claim 14, wherein the first portion of alumina particles has a particle size of, or greater than, 3 μm and up to 5 μm.

16. The catalyst according to claim 14, wherein at least 20 wt% but less than 100 wt% of the alumina particles have a particle size of, or less than, 2 µm, wherein said wt% is relative to the weight of alumina in the carrier.

17. The catalyst according to claim 14, wherein the carrier possesses a pore size distribution having a peak pore size of, or less than, 2 µm.

18. The catalyst according to claim 14, wherein no more than 40% of the pores have a pore size of or less than 1 µm.

19. A method for the vapor phase conversion of ethylene to ethylene oxide in the presence of oxygen, the method comprising reacting a reaction mixture comprising ethylene and oxygen in the presence of a catalyst comprising:

a) a carrier comprising alumina containing a first portion of alumina particles having a particle size of, or greater than, 3 µm and up to 6 µm, and a second portion of alumina particles having a particle size less than 1 µm, wherein at least 20 wt% but less than 100 wt% of the alumina particles have said particle size less than 1 µm, wherein said wt% is relative to the weight of alumina in the carrier;

b) a catalytic amount of silver deposited on and/or in said carrier; and c) a promoting amount of rhenium deposited on and/or in said carrier.

20. The method according to claim 19, wherein the first portion of alumina particles has a particle size of, or greater than, 3 µm and up to 5 µm.

21. The method according to claim 19, wherein at least 20 wt% but less than 100 wt% of the alumina particles have a particle size of, or less than, 2 µm, wherein said wt% is relative to the weight of alumina in the carrier.

22. The method according to claim 19, wherein the carrier Possesses a pore size distribution having a peck pore size of, or less than, 2 µm.

23. The method according to claim 19, wherein no more than 40% of the pores have a pore size of or less than 1 µm.

* * * * *